United States Patent
Ruppert et al.

(10) Patent No.: US 9,144,533 B2
(45) Date of Patent: Sep. 29, 2015

(54) DENTAL ADHESIVE AGENT FOR HIGH-PERFORMANCE POLYMERS

(71) Applicant: Heraeus Kulzer GmbH, Hanau (DE)

(72) Inventors: Klaus Ruppert, Maintal (DE); Alfred Hohmann, Schmitten (DE)

(73) Assignee: Heraeus Kulzer GmbH, Hanau (DE)

( * ) Notice: Subject to any disclaimer, the term of this patent is extended or adjusted under 35 U.S.C. 154(b) by 0 days.

(21) Appl. No.: 13/967,550

(22) Filed: Aug. 15, 2013

(65) Prior Publication Data

US 2014/0053965 A1    Feb. 27, 2014

(30) Foreign Application Priority Data

Aug. 21, 2012  (DE) .......................... 10 2012 016 418

(51) Int. Cl.
    *A61K 6/083*    (2006.01)
    *A61K 6/00*    (2006.01)

(52) U.S. Cl.
    CPC ............... *A61K 6/083* (2013.01); *A61K 6/0023* (2013.01)

(58) Field of Classification Search
    CPC ...................................... A61K 6/083
    USPC .................................. 156/61, 325
    See application file for complete search history.

(56) References Cited

U.S. PATENT DOCUMENTS

| | | | |
|---|---|---|---|
| 4,654,006 A | 3/1987 | Kusano et al. | |
| 4,952,614 A | 8/1990 | Reiners et al. | |
| 5,127,834 A | 7/1992 | Hasegawa et al. | |
| 5,243,006 A | 9/1993 | Nakabayashi et al. | |
| 6,121,344 A * | 9/2000 | Angeletakis et al. | 523/116 |
| 7,081,485 B2 | 7/2006 | Suh et al. | |
| 7,214,262 B2 | 5/2007 | Hurwitz et al. | |
| 2008/0213718 A1 | 9/2008 | Abels et al. | |
| 2009/0048366 A1 * | 2/2009 | Torii et al. | 523/116 |
| 2010/0112518 A1 | 5/2010 | Engelbrecht et al. | |
| 2010/0139670 A1 | 6/2010 | Lesniak | |
| 2011/0196062 A1 * | 8/2011 | Craig | 523/116 |
| 2012/0123012 A1 | 5/2012 | Rheinberger et al. | |
| 2012/0196249 A1 | 8/2012 | Maletz | |
| 2013/0017511 A1 * | 1/2013 | Kashiwabara et al. | 433/173 |

FOREIGN PATENT DOCUMENTS

| | | |
|---|---|---|
| DE | 37 03 080 A1 | 1/1988 |
| DE | 37 03 120 A1 | 1/1988 |
| DE | 3 610 316 C2 | 6/1990 |
| DE | 69 025 592 T2 | 8/1996 |
| DE | 100 43 174 A1 | 3/2002 |
| DE | 10 2006 050 153 A1 | 5/2008 |
| DE | 11 2006 001 049 T5 | 12/2008 |
| DE | 10 2011 003 289 A1 | 8/2012 |
| WO | 2008113541 A2 | 9/2008 |

OTHER PUBLICATIONS

Office Action issued by the German Patent Office dated Apr. 4, 2014.

* cited by examiner

*Primary Examiner* — Daniel Lee
(74) *Attorney, Agent, or Firm* — Norris McLaughlin & Macus PA

(57) ABSTRACT

The invention relates to a method for the production of an adhesive bond between (a) the surface of dental subframes based on high-performance polymers, and (b) dental composites, by
A at least creating retentive anchoring by means of mechanical pre-treatment of the surface of each subframe;
B application of a low viscous, or free-flowing adhesive agent containing a monomer mixture of polymethyl methacrylate, methyl methacrylate, at least one bifunctional methacrylate-based cross-linking monomer, initiator(s), and optionally stabilizers and other additives, including
  (i) wetting of the surface,
  (ii) penetration into the depressions which are present, and
  (iii) formation of a dispersion layer or a film;
C at least partially curing the dispersion layer or the film in step B; and
D applying a dental composite or an opaque onto the product in step C.

9 Claims, No Drawings

DENTAL ADHESIVE AGENT FOR HIGH-PERFORMANCE POLYMERS

The invention relates to adhesive agents, and to the production of an adhesive bond between high-performance polymers and dental composites, particularly to dental veneer composites.

BACKGROUND OF THE INVENTION

Prosthetic work, such as crowns or bridges, for example, requires a supportive substructure in many cases to ensure mechanical stability. Typically, these subframes consist of metal alloys or of metal-free materials such as, by way of example, $ZrO_2$, $Al_2O_3$, or high-performance polymers such as PEEK. In order to impart an aesthetic appearance to the tooth restoration on such a subframe structure, the same is given a veneer of a dental composite in the color of the tooth; or in the case of metal subframes, a tooth-colored ceramic. An adhesive agent is typically used to ensure a durable bond.

First, the surface is mechanically treated, typically by means of sand jets. An adhesive layer is then applied first to the sand-blasted subframe, and said adhesive layer produces a bond between the subframe surface and the subsequent (meth-) acrylate-based layers. Next, a layer of a relatively transparent, fluid material is applied on the adhesive agent, wherein said material can flow into the dead spaces in the undercuts, and can fill these in. It must be ensured in the process that the material cures sufficiently in this space. Next, one or more layers of opaque material can be applied on this fluid layer, to conceal the subframe with color. The actual veneer composite then forms the completion of the layered construction.

WO 2008113541A2 relates to conditioning agents which are suitable for polymers selected from the group containing polyarylates, polyarylene sulfides, polysulphones, liquid crystal polymers, polyimides, polyether imides, polyamide imides, and polyaryl ether ketones. The conditioning agents contain an adhesive and a higher boiling point solvent with dipole character, the latter selected from the group containing dimethyl sulfoxide, phenol, diphenyl sulfone, cyclohexanone, acetyl acetone, and ethylene glycol. The use thereof comprises the application of the conditioning agent onto at least a part of the surface of the mold body, allowing the conditioning agent to work in, and optionally applying a curable mixture onto the surface of the mold body conditioned by means of the conditioning agent. The examples relate to DMSO-containing conditioning agents. DMSO is not without problems according to the safety data sheet thereof, and is not suitable for use in the mouth[1]:

[1] product name: dimethylsulfoxide (DMSO)

SUMMARY OF THE INVENTION

A method is provided by means of which it is possible to produce a durable bond between a high-performance polymer such as PEEK, for example, and a (meth-) acrylate-based veneer composite. Solvents which are potentially seen as problematic should be avoided.

DETAILED DESCRIPTION

In particular, the surface of the subframe is mechanically treated, particularly by sandblasting, to clean and activate the surface, and to create retentive anchoring. The blasting abrasive is preferably 110 μm corundum.

Next, a light-curable, low viscous or free-flowing, methacrylate-based component (adhesive agent and/or conditioning means) is applied, which forms a thin film on the subframe surface, and also leads to a retentive adhesive bond after curing. It contains PMMA (polymethyl methacrylate), MMA (methyl methacrylate), bifunctional methacrylate-based monomers, e.g. UDMA (urethane dimethacrylate), and photoinitiator(s), as well as optionally stabilizers and inorganic pigments. In addition, means for adjusting the viscosity can likewise be optionally included, such as fine silicas which can be silanized in a manner known to a person skilled in the art.

The general recipe of such an adhesive agent is, by way of example, as follows (in percent by weight):

| | |
|---|---|
| 60-70% | MMA |
| 5-15% | PMMA |
| 20-30% | UDMA |
| 0.1 to 5% | photoinitiator, preferably from the group of acylphospine photoinitiators |
| 0.05 to 5% | stabilizer, preferably from the group of sterically hindered phenols, such as 2,6-ditertiary-butyl-4-methylphenol. |

The polymethyl methacrylate can be included in the preparation of the adhesive agent as such, preferably in the form of polymerisate pearls with a particle size of 10-150 micrometers, or as a solution (or partial solution) having methyl methacrylate monomers. A polymethyl methacrylate is preferred in this case which has an average molecular weight of 120,000-200,000.

For the adhesive layer applied in the process, a layer thickness of 0.5 to 2.5 μm, for a single application, and 4.5 to 7.5 μm, for a double application of the adhesive agents, has proven advantageous. The center of this range is particularly preferred, meaning 1-2 μm for a single application, and 5 μm for a double application. In the case of a triple application, layer thicknesses of 10 μm are achieved.

The viscosity of the adhesive agent is preferably in the range from approx. 10-30 mPas at 23° C. For the means used to adjust the viscosity, in addition to the monomers used, oligomers and polymers can also be used, as well as additives such as silicas, and primarily fumed silicas. The subframe, e.g. based on PEEK, can be masked after treatment with the adhesive agent, for example by means of a veneer composite. Examples for these include Signum® composite or Signum® matrix from the Heraeus Kulzer company.

The curing is preferably carried out by a curing mechanism in the UV or visible light spectral region. The use of new, IR-sensitive initiators is also possible.

An additional advantage of the method according to the invention is a simple processing, and no reliance on dangerous and/or toxic chemicals (as suggested in WO 2008113541 A1, for example). In addition, no exposure time is necessary for the coating.

For the dental composite, the conventional dental composite mixtures based on monomer mixtures and fillers can be contemplated.

Examples of suitable monomers are the conventional (meth)acrylates used in the dental field, for example in monomeric form, such as ethylene glycol dimethacrylate EDMA, diethylene glycol dimethacrylate, triethylene glycol dimethacrylate TEGDMA, glycerol dimethacrylate GDMA, glycerol trimethacrylate, trimethylol propane trimethacrylate, pentaerythritol dimethacrylate, pentaerythritol trimethacrylate, pentaerythritol tetramethacrylate, derivatives of bisphenol A, such as bisphenol A dimethacrylate and bisphenol A diglycol dimethacrylate, urethane methacrylate obtained from diisocyanates and hydroxyl alkyl methacrylates, and reaction products of polyols, diisocyanates, and hydroxyl alkyl methacrylates according to DE 37 03 080 A1 or DE 37 03 120 A1; $C_{1-12}$-, and preferably $C_{1-4}$-alkyl methacrylates such as methyl methacrylate, ethyl methacrylate, n-propyl methacrylate, isopropyl methacrylate, n-butyl methacrylate, and t-butyl methacrylate, hydroxyl alkyl $C_{1-4}$-methacrylates such as 2-hydroxyethyl methacrylate, 2-hydroxypropyl methacrylate, diethylene glycol monomethacrylate, triethylene glycol monomethacrylate, alkoxy $C_{1-4}$-alkyl methacrylates such as 2-methoxy ethyl methacrylate, 3-methoxy butyl methacrylate, and ethyl triglycol methacrylate. Suitable monomers thereof are in each case the monomers themselves, polymerizable prepolymers made therefrom, and mixtures of the same.

Suitable fillers are known to a person skilled in the art. Examples are inert and reactive dental glasses such as barium silicate glass, strontium silicate glass, borosilicate glass, and fluoroaluminosilicate glass, or fumed, precipitated, or fossil silicates. Mixtures are preferably used which have filler particles of different sizes, with particle sizes between 0.001 and 100 µm.

Also suitable are micro- and/or nano-scale fillers, such as by way of example metal, metalloid, or mischmetal oxides, silicates, nitrides, sulfates, titanates, zirconates, stannates, tungstenates, silicon dioxide, or mixtures of these compounds, as well as spherical fillers, powders of further glasses or glass ceramics and the mixtures thereof, and also filled or unfilled splinter polymerisates and/or pearl polymerisates.

The fillers can be surface-modified, particularly organic surface-modified, and for example silanized. A surface-modified filler can have functional groups on its surface which can react chemically, and preferably as radicals, or which have a high affinity to the polymer matrix formed by the monomers, wherein the filler is preferably surface-modified with silane which carries reactive acrylate or methacrylate groups.

The method according to the invention particularly serves the purpose of creating adhesion between the subframe made of a high-performance polymer, and the layers, of so-called opaque (which is heavily white-pigmented composite for the purpose of hiding the subframe colors), applied on the adhesive agent layer. However, dental composites can also be directly applied.

The method according to the invention is characterized by its simplicity and efficiency: application, curing, no long waiting for exposure time, the next layer (e.g. opaque dental composite) can be immediately applied, and a strong, durable bond results [sic].

For the high-performance polymer, polyether ether ketone (PEEK), polyether ketone ketone (PEKK), polyoxymethylene (POM), and polyamides such as the Zellamid® types described thoroughly in the examples, can be considered.

The following examples show that the adhesion values are best if a treatment is made twice with the adhesive agent according to the general recipe above. Three or more applications are likewise possible. The examples serve to explain the invention in greater detail. Information given in fractions and percents is based on weight unless otherwise specified, as is true for the rest of the description.

EXAMPLES

After the subframe material is sandblasted with 110 µm corundum, washed with fully desalinated water, and dried with oil-free air, the adhesive agent is applied 2× and irradiated for 90 sec. with the Heraflash® laboratory curing light (Heraeus Kulzer company). Next, 2 layers of Signum® opaque F (Heraeus Kulzer company) are applied, and each cured for 90 sec. with the Heraflash®. A layer of Signum® composite (Heraeus Kulzer company) forms the completion, optionally in various colors, which are cured for 90 sec. and then finally cured again for 180 sec. for the purpose of tempering.

Test blocks produced with this process gave the following values for the testing of the shear bond strength pursuant to ISO 10477 (Table A):

| Subframe material | Vestkeep/Evonik | | |
|---|---|---|---|
| Adhesive agent | x | x | 1x |
| Signum opaque F | x | 2x | 2x |
| Signum composite | | yes | |
| TWL (5° C./55° C.) | | 5000 | |
| Shear bond strength [MPa] | 2.6 | 14.5 | 18.5 |

According to ISO 10477, a shear bond strength of at least 5 MPa must be reached when no macromechanical retentions are used. According to ISO 10477, the test blocks are subjected to a dynamic temperature load of 5000 cycles prior to the shearing test.

Surprisingly, the adhesion using the adhesive agent according to the invention is more than satisfactory, and lies significantly above the requirements of the norm.

The adhesive agent according to the invention is also suitable for other high-performance polymers besides PEEK. This can be seen in the following Table B, which shows that the adhesion for various different polymers is far above the norm, and therefore is more than sufficient:

| Subframe material | Zellamid 202 (PAG) | Zellamid 900 (POM) | Zellamid 202XN | Bioloren |
|---|---|---|---|---|
| Adhesive agent | 2x | 2x | 2x | 2x |
| Signum opaque F | 2x | 2x | 2x | 2x |
| Signum composite | yes | yes | yes | yes |
| TWL (5° C./55° C.) | 5000 | 5000 | 5000 | 5000 |
| Shear bond strength [MPa] | 19.5 | 18.6 | 18.5 | 22.8 |

These values are up to 46% higher than those in the prior art, WO 2008113541A2 (where the values were 15.2 MPa for dentanium, a composite material based on PEEK).

The individual high-performance polymers in the table above are available commercially and described as follows, according to the provisions of the manufacturer:

Zellamid® 900/POM-C (Zell-Metall Ges.mbH. Engineering Plastics, Kaprun—Austria)

POM-C is a semicrystalline thermoplastic produced from acetal copolymerisate granulate, and is characterized by a low coefficient of friction and good wear properties. As water absorption is very minimal, dimensional stability is much better than that of polyamides. POM is resistant to numerous chemicals and also solvents. POM provides high strength and stiffness coupled with easy machineability.

ZELLAMID® 900 is also noted for its high mechanical strength, heat resistance and good antifriction properties. ZELLAMID® 900 is according to ASTM D 6100 porosity free and most formulations are approved for contact with food (BfR, FDA compliant). Good for parts which need to be dimensionally stable even when exposed to humid or wet environments. POM-C offers better hot water resistance than POM-H (the homopolymer).

ZELLAMID® 202 (Zell-Metall Ges.mbH. Engineering Plastics, Kaprun—Austria)

ZELLAMID® 202 is a tough material with high resistance to abrasion and impact, based on polyamide 6 (PA 6). PA 6 is commonly used as a substitution material for bronze, aluminum and other non-ferrous metals, as it has significant weight advantages. ZELLAMID® 202 therefore has a specific gravity of 1.15 g/cm$^3$ and bronze has 8.8 g/cm$^3$, making the comparative volume price very attractive. Using ZELLAMID® 202 also reduces lubrication requirements and is non-abrasive to mating surfaces [sic]. It features good mechanical properties. PA 6 can absorb up to 8% water (by weight) under humidity or submerged in water. This increases the excellent shock and vibration resistance but can also lead to dimensional changes. Mechanical, electrical and dimensional properties are accordingly influenced by moisture absorption. ZELLAMID® 202 is approved for contact with food (BfR, FDA).

ZELLAMID® 202 XN (Zell-Metall Ges.mbH. Engineering Plastics, Kaprun—Austria):

This polyamide is a high tech material, developed with Zell-Metall Engineering Plastic's brand-new technology (nanotechnology). This uniquely reinforced PA 6 outperforms standard PA 6, PA 6.6 and in several properties PA 6.6 with 30% glass fibers. ZELLAMID® 202 XN has an elevated service temperature of 140° C. with an HDT of 168° C. It features increased mechanical strength with a tensile modulus of elasticity of 4200 MPa (ISO 527, dry). Reduced water absorption ensures better dimensional stability. This product is applicable for direct food contact (BfR, FDA) and offers in comparison to glass-filled nylons approx. 15% lower specific gravity resulting in less volume costs. The flame-retardant effect of the nanoparticles brings an improvement of the behavior of the material in fire.

ZELLAMID® 202 XN is the alternate choice for many applications, where other products are lacking the necessary properties (e.g. service temperature) or standard materials are too soft—such as PTFE—or too expensive, such as PEEK. In comparison to glass filled polyamides, this material is easy to machine as no preheating or usage of diamond tipped tools is necessary.

VESTAKEEP® PEEK products for medical technology (Evonik Industries AG, Essen, Germany)

The products VESTAKEEP® M2G, VESTAKEEP® 12G, VESTAKEEP® M4G, VESTAKEEP® 14G, and the powder VESTAKEEP® M4P are available for applications in medical technology. The recipe of these products is tuned for high biocompatibility; additionally, batch testing in vitro for cytotoxicity per EN ISO 10993-5 offers additional safety.

The invention claimed is:

1. A method for the production of an adhesive bond between (a) the surface of dental subframes based on polymers comprising polyether ether ketone (PEEK), polyether ketone ketone (PEKK), polyoxymethylene (POM), and/or polyamide and (b) dental composites, by A at least creating retentive anchoring by means of mechanical pre-treatment of the surface of each subframe; wherein the mechanical treatment is carried out by sandblasting;

B application of a low viscous, or free-flowing adhesive agent containing a monomer mixture of polymethyl methacrylate, methyl methacrylate, at least one bifunctional methacrylate-based cross-linking monomer, initiator(s), and optionally stabilizers and other additives, wherein the adhesive agent has no solvent and, wherein the adhesive agent has a viscosity of 10-30 mPas at 23° C., including (i) wetting of the surface,
    (ii) penetration into the retentive anchoring, and
    (iii) formation of a dispersion layer or a film;

C at least partially curing the dispersion layer or the film in step B; and

D applying a dental composite or an opaque onto the cured dispersion or film in step C.

2. A method according to claim 1, wherein the adhesive agent contains UDMA (urethane dimethacrylate), MMA (methyl methacrylate), PMMA (polymethyl methacrylate), photoinitiator(s), and stabilizer(s).

3. A method according to claim 2, wherein the PMMA is present partially dissolved in MMA.

4. A method according to claim 1, wherein the adhesive agent contains a means for adjusting the viscosity.

5. A method according to claim 1, wherein the adhesive agent contains fine precipitated silica or fumed silica.

6. A method according to claim 1, wherein the sandblasting is carried out with 110 μm corundum.

7. A method according to claim 1, wherein the adhesive agent additionally contains inorganic pigments.

8. A method according to claim 1, wherein the application of dental composite or opaque in D occurs in multiple layers.

9. A method according to claim 1, wherein no waiting time is observed between C and D.

\* \* \* \* \*